United States Patent
Hoelscher et al.

(10) Patent No.: US 9,915,715 B2
(45) Date of Patent: Mar. 13, 2018

(54) METHOD AND APPARATUS FOR MAGNETIC RESONANCE IMAGING

(71) Applicant: Siemens Aktiengesellschaft, Munich (DE)

(72) Inventors: Uvo Hoelscher, Erlangen (DE); Dominik Paul, Bubenreuth (DE)

(73) Assignee: Siemens Aktiengesellschaft, Munich (DE)

(*) Notice: Subject to any disclaimer, the term of this patent is extended or adjusted under 35 U.S.C. 154(b) by 40 days.

(21) Appl. No.: 15/061,081

(22) Filed: Mar. 4, 2016

(65) Prior Publication Data

US 2016/0259021 A1    Sep. 8, 2016

(30) Foreign Application Priority Data

Mar. 6, 2015    (DE) .................. 10 2015 204 116

(51) Int. Cl.
| | |
|---|---|
| *G01V 3/00* | (2006.01) |
| *G01R 33/483* | (2006.01) |
| *A61B 5/055* | (2006.01) |
| *G01R 33/48* | (2006.01) |
| *G01R 33/561* | (2006.01) |
| *G01R 33/54* | (2006.01) |
| *A61B 5/00* | (2006.01) |

(52) U.S. Cl.
CPC .......... *G01R 33/483* (2013.01); *A61B 5/055* (2013.01); *A61B 5/7485* (2013.01); *G01R 33/4822* (2013.01); *G01R 33/543* (2013.01); *G01R 33/561* (2013.01); *A61B 5/7257* (2013.01); *A61B 2576/026* (2013.01)

(58) Field of Classification Search
CPC .................................................. G01R 33/483
USPC ......................... 324/309, 307, 306
See application file for complete search history.

(56) References Cited

U.S. PATENT DOCUMENTS

| | | | |
|---|---|---|---|
| 8,199,168 B2* | 6/2012 | Virtue | A61B 6/032 345/642 |
| 8,664,953 B2 | 3/2014 | Morita | |
| 2010/0052676 A1 | 3/2010 | Sugiura | |
| 2012/0262171 A1* | 10/2012 | Weber | G01R 33/4833 324/309 |

OTHER PUBLICATIONS

Grodzki et al; "Ultrashort Echo Time Imaging Using Pointwise Encoding Time Reduction With Radial Acquisition (PETRA)"; Magnetic Resonance in Medicine; vol. 67; pp. 510-518, (2012).

* cited by examiner

*Primary Examiner* — Louis Arana
(74) *Attorney, Agent, or Firm* — Schiff Hardin LLP

(57) ABSTRACT

In a method and apparatus for magnetic resonance imaging of an examination object, a control computer is provided with a designation of a first recording region, which is cuboidal. The computer automatically determines a second recording region that represents an adjustment of the first recording region such that the second recording region is cube-shaped. Magnetic resonance scan data are acquired from the entire second recording region. Magnetic resonance image data are reconstructed from the acquired magnetic resonance scan data. An image region of the magnetic resonance image data is supplied in electronic form from the computer.

10 Claims, 3 Drawing Sheets

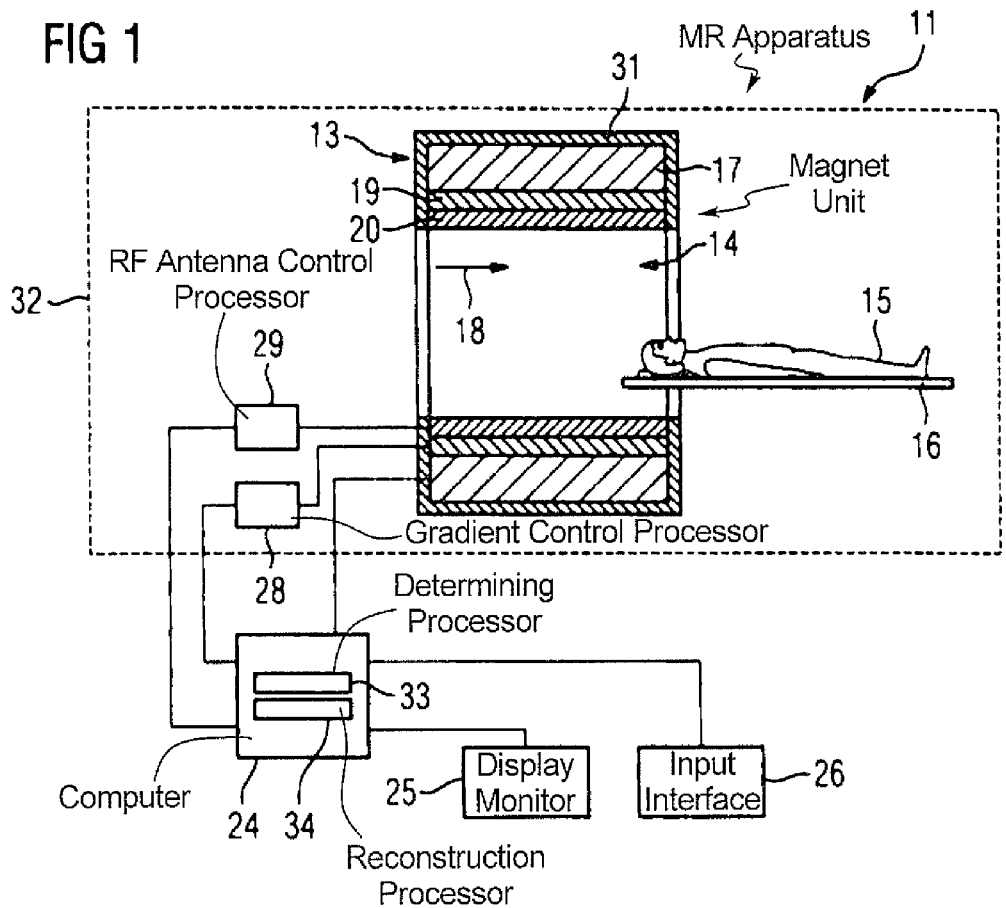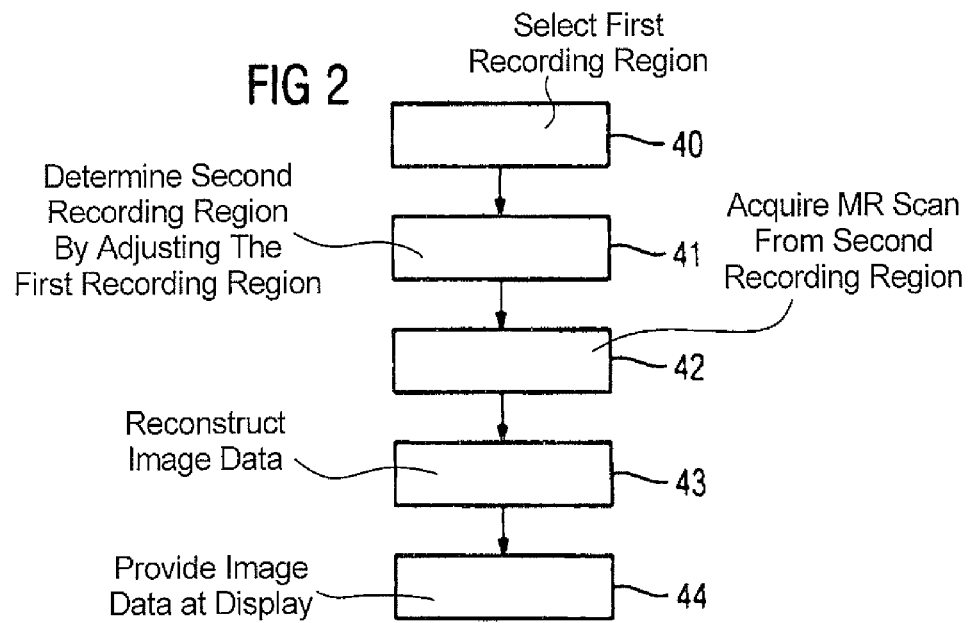

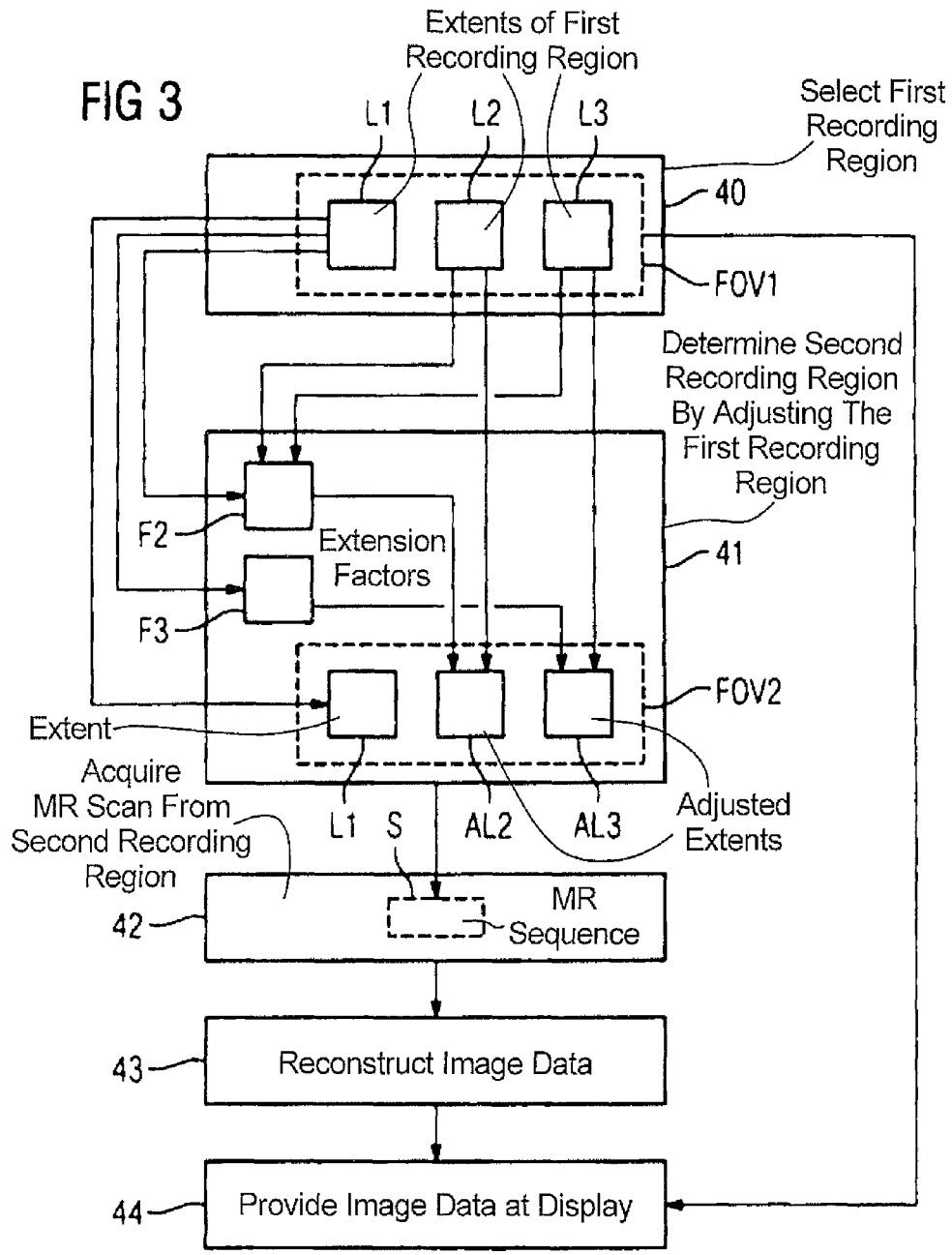

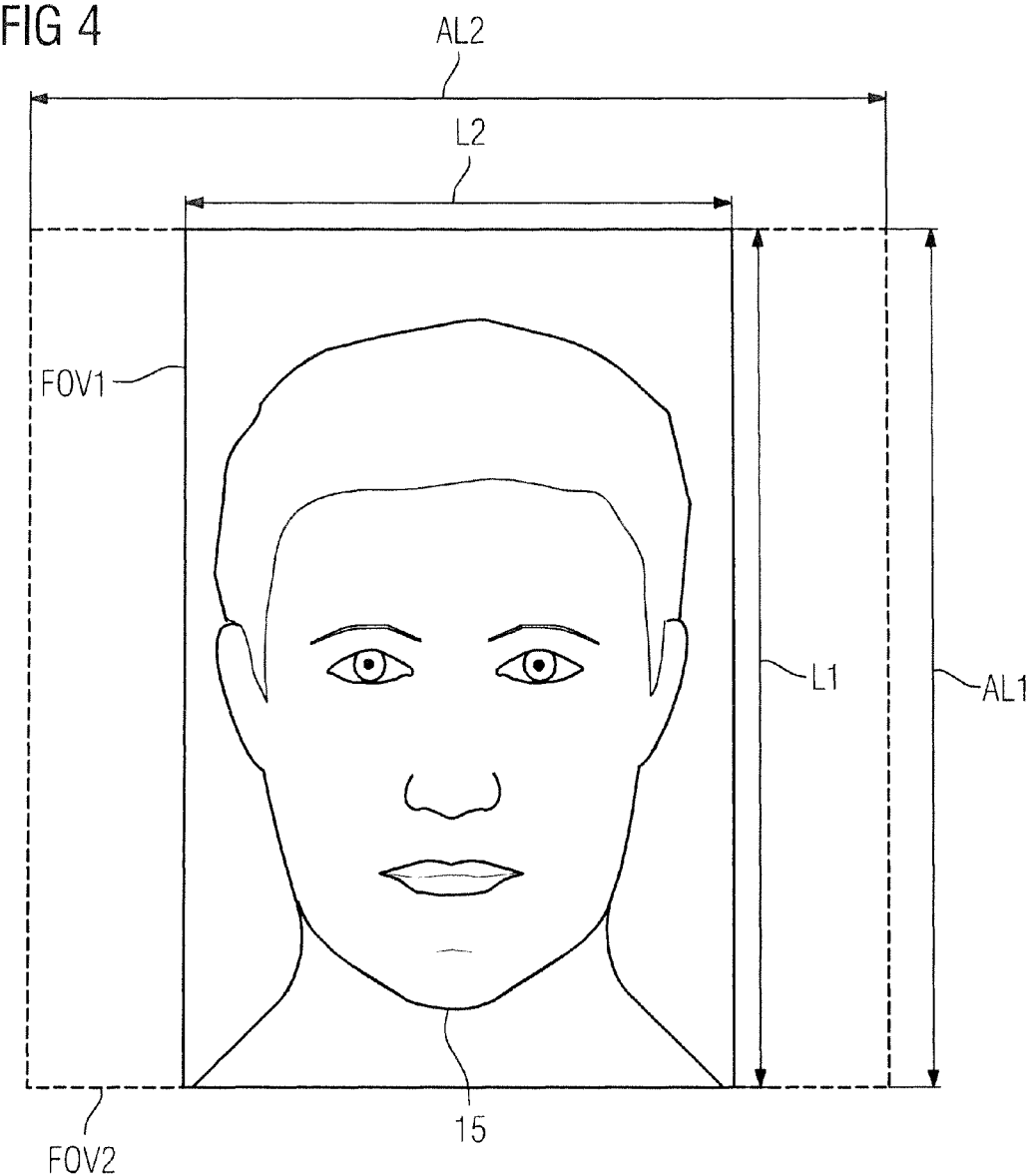

METHOD AND APPARATUS FOR MAGNETIC RESONANCE IMAGING

BACKGROUND OF THE INVENTION

Field of the Invention

The invention concerns a method for magnetic resonance imaging, a magnetic resonance apparatus, and to a non-transitory, computer-readable storage medium encoded with programming instructions for implementing such a method.

Description of the Prior Art

In a magnetic resonance apparatus, also called a magnetic resonance tomography system, the body of an examination person, in particular a patient, to be examined is conventionally exposed with by a basic field magnet to a relatively high basic magnetic field, for example of 1.5 or 3 or 7 tesla. In addition, gradient switching operations occur with the use of a gradient coil arrangement. Radio frequency pulses, for example excitation pulses, are then emitted by a radio-frequency antenna arrangement by means of suitable antenna devices, and this leads to the nuclear spins of specific atoms, excited in a resonant manner by these radio-frequency pulses, being tilted by a defined flip angle with respect to the magnetic field lines of the basic magnetic field. When the nuclear spins relax, radio-frequency signals, known as magnetic resonance signals, are radiated that are received by suitable radio-frequency antennae and then processed further. Finally, the desired image data can be reconstructed from the raw data acquired in this way.

For a specific scan, a specific magnetic resonance sequence, also called a pulse sequence, is to be emitted that includes a sequence of radio-frequency pulses, for example excitation pulses and refocusing pulses, and appropriate gradient switching operations that are to be emitted in a coordinated manner in various gradient axes in various directions. At a time appropriate therewith readout windows are set, and these specify the periods in which the induced magnetic resonance signals are detected.

An important setting of the magnetic resonance sequence is the choice of a recording region from which the magnetic resonance signals for generating the magnetic resonance images are to be acquired. The recording region is typically manually chosen by a user via an input interface. The choice of recording region typically includes defining a position and/or geometry and/or dimensions of the recording region. The recording region is typically chosen on a topogram, known as a localizer image.

SUMMARY OF THE INVENTION

An object of the invention is to enable advantageous determination of a recording region for the magnetic resonance imaging.

The inventive method for magnetic resonance imaging of an examination object by operation of a magnetic resonance apparatus has the following steps.

A first recording region is selected, which is cuboidal. A second recording region is automatically determined in a computer, which represents an adjustment of the first recording region such that the second recording region is cube-shaped. Magnetic resonance scan data are acquired from the entire second recording region. Magnetic resonance image data and reconstructed by the computer from the magnetic resonance scan data. An image region of the magnetic resonance image data is made available from the computer in electronic form as a data file.

The examination object can be a patient, training person, an animal or a phantom. The recording region, also called an examination region or a recording volume (field of view, FOV), is a volume that is mapped by the magnetic resonance image data. The recording region is three-dimensional. The recording region is Cartesian. The first recording region describes a section of the examination object that is of interest to the magnetic resonance imaging. The first recording region is typically fixed by a user, for example on a topogram (localizer). The user can manually define the limits of the first recording region via the input interface. The user can also define, for example, a number of slices to be recorded and/or a resolution for the first recording region. Of course the recording region can alternatively or additionally be defined automatically, such as on the basis of a chosen protocol.

The definition of the first recording region as being cuboidal means that the first recording region has twelve edges, wherein four first edges of the twelve edges are parallel to each other and of equal length, four second edges of the twelve edges are parallel to each other and of equal length and four third edges of the twelve edges are parallel to each other and of equal length. In particular, the four first edges are longer than the four second edges and/or the four third edges. The four second edges can also be longer than the four third edges. In particular, the angles between the first edges and the second edges, or between the first edges and the third edges are right angles. The definition of the second recording region as being cube-shaped means that all edges of the second recording region are of equal length. In particular, the second recording region has the same extent in all three directions.

The second recording region is automatically determined such that the first recording region is a sub-part of the second recording region. The second recording region can completely encompass the first recording region. The second recording region thus is larger than the first recording region. In addition to the first recording region, the second recording region can have at least one extension region, which, when combined with the first recording region, produces the second recording region. This at least one extension region is advantageously chosen such that the first recording region, in combination with the at least one extension region, is cube-shaped. For this purpose, the at least one extension region preferably is itself cuboidal. The first recording region is stretched by an extension factor in at least one direction, advantageously in a second direction by potentially a different extension factor, producing the cube-shaped second recording region. It should be noted that only the creation of the second recording region is intended with the adjustment of the first recording region to the second recording region. The first recording region should itself be left unchanged. For example, the first recording region, as described below, can be the image region of the magnetic resonance image data that is to be represented in the computer output. Alternatively, it is also conceivable in specific cases for the second recording region to be smaller in at least one direction than the first recording region.

The process of automatic adjustment of the first recording region to the cube-shaped second recording region has the advantage that, when choosing the first recording region, the user does not have to take care to choose the first recording region so as to be cube-shaped. The magnetic resonance sequence for acquiring the magnetic resonance scan data can require a cube-shaped recording region, as described in more detail below. The automatic adjustment of the first recording region chosen by the user to the cube-shaped second recording region ensures that the magnetic resonance scan data are acquired from the required cube-shaped, second recording region. In this way the user can choose the desired first recording region particularly easily without having to be concerned with the required cube-shaped design of the recording region. In this way even inexperienced users can correctly define the recording region for the magnetic resonance imaging. Furthermore, the user can choose the first recording region, in particular in all three directions, as he or she wishes and without restrictions. This can be particularly advantageous if a body region of the patient is to be mapped that has different side lengths, for example a head region of the patient.

According to inventive method the magnetic resonance scan data is acquired from the entire second recording region. Acquisition of magnetic resonance scan data from the second recording region includes acquisition of raw data and/or magnetic resonance signals from the entire second recording region. Magnetic resonance scan data are typically acquired by the application of phase coding gradients and frequency coding gradients and recording of the resulting magnetic resonance signals by a radio-frequency coil. The magnetic resonance signals read out during acquisition of the magnetic resonance scan data are typically stored in a memory representing k-space. The magnetic resonance scan data are typically only the raw data that contain the recorded magnetic resonance signals. The magnetic resonance scan data are therefore not typically directly available to an expert for diagnosis.

Instead, using the magnetic resonance scan data, magnetic resonance image data are reconstructed, which can be displayed on a display monitor and/or can be displayed for an expert in order to create a diagnosis. Reconstruction of the magnetic resonance image data from the magnetic resonance scan data includes generation of magnetic resonance images stored in the image domain from the magnetic resonance signals stored in k-space. The magnetic resonance image data can be reconstructed in a manner known to those skilled in the art, for example using a Fourier transformation. The magnetic resonance image data can then be reconstructed using all of the acquired raw data from the second recording region. The magnetic resonance image data can map the entire second recording region, which is cube-shaped, in this way.

Furthermore, according to the inventive method only one image region of the magnetic resonance image data, corresponding to a section of the magnetic resonance image data, is included in the output. In specific cases the image region can also correspond to all of the magnetic resonance image data. The image region corresponds to the first recording region, for example according to its spatial dimensions and/or spatial location and/or spatial limitations, as described in more detail below. Therefore, during image reconstruction, firstly magnetic resonance image data are reconstructed from the entire second recording region, and thereafter only the portion of the magnetic resonance image data, the image region, that is of interest to the user is emitted in the output. The portion of the magnetic resonance image data which is not part of the image region is therefore excised and discarded before the output. The automatic selection of the image region from the magnetic resonance image data advantageously takes place automatically in the background. The user does not realize that magnetic resonance scan data are acquired from a larger second recording region, since only the image region of the magnetic resonance image data is supplied in the output.

Emitting the image region as an output in electronic form can be displaying the image region on a display monitor for a user and/or storing the image region in a database. In the case of displaying the image region, the image region is provided as an output for the user on a display monitor. This approach has the advantage that the user, for example a radiologist, is supplied only with the image region of the magnetic resonance image data that is of interest to the user. The user can therefore extract diagnostically relevant information from the displayed image region more quickly. The user does not have to leaf through a large number of empty slices which contain only noise, artifacts or clinically irrelevant regions until the image content of the image region that is actually desired appears. Such a large number of empty slices can result due to the extension of the first recording region to the cube-shaped second recording region. In this way displaying of the disruptive empty slices can be advantageously avoided by selective supplying of the image region of the magnetic resonance image data. In this way operator convenience can be increased for the diagnosing expert.

Alternatively or additionally, supplying the image region can be storing the image region in a database, for example an image database, an image viewing database or a PACS network. The fact that then only one relevant sub-part of the magnetic resonance image data is stored reduces the data load in the data volume and/or shortens access times to the database. At the same time, the time for further processing of the magnetic resonance image data can be significantly shortened by the selective storing of the image region of the magnetic resonance image data.

At the same time, the fact that the magnetic resonance scan data is acquired from the larger second recording region can lead to a signal-to-noise ratio (SNR) of the magnetic resonance image data being increased. This fact is based on the consideration that more data points are acquired during acquisition of the magnetic resonance scan data. Even if a portion of the magnetic resonance image data, namely the portion of the magnetic resonance image data that does not correspond to the image region, is discarded during or after reconstruction of the magnetic resonance image data, the image quality, in particular the signal-to-noise ratio, of the image region is increased.

Furthermore, the choice of a cube-shaped second recording volume can ensure that the magnetic resonance scan data is acquired with equidistant sampling points. In this way, for example, aliasing of signal-generating hardware components, for example coils, patient bed or headphones, and/or patient anatomy, for example shoulders in the case of imaging of the head, in the image region of the magnetic resonance image data can be avoided. Freedom from artifacts in the magnetic resonance image data can be ensured in this way.

Since it proceeds primarily in the background without the user's knowledge, the inventive approach does not require any, or only a slight, adjustment of the user interface in order to plan the magnetic resonance imaging. The automatic extension of the first recording region to the cube-shaped second recording region can also be carried out by data elements, for example oversampling factors, already included in a planning program.

In an embodiment, a magnetic resonance sequence that requires a cube-shaped recording region for acquisition of the magnetic resonance scan data is used. A cube-shaped recording region, from which the magnetic resonance scan data are acquired according to the magnetic resonance sequence, is then necessary for the recording method that is used by the magnetic resonance sequence. Use of a merely cuboidal recording region with at least partially different dimensions of the recording region can lead to problems in such magnetic resonance sequences, for example to non-functioning of the magnetic resonance sequence, a reduced image quality and/or to artifacts, for example disruptive aliasing of magnetic resonance signals in the image region. A magnetic resonance sequence of this kind can use, for example, three-dimensional star-shaped data acquisition in k-space that is to be recorded (known as "spiky ball" acquisition). The magnetic resonance sequence thus can cause spokes of the same length, in particular with equidistant sampling points, to be acquired in all directions starting from a center of k-space that is to be recorded. A magnetic resonance sequence of this kind is also known as a pointwise encoding time reduction with radial acquisition (PETRA) sequence. The magnetic resonance sequence that is used to acquire the magnetic resonance scan data can therefore be a PETRA sequence. The PETRA sequence is known, for example, from Grodzki et al., "Ultrashort echo time imaging using pointwise encoding time reduction with radial acquisition (PETRA)", Magn Reson Med, 2012, 67(2), 510-518. If a magnetic resonance sequence of this kind is used to acquire the magnetic resonance scan data, the described approach is therefore particularly advantageous since the required cube-shaped recording volume for the magnetic resonance sequence can be automatically ensured in this way. It can also be achieved by the preventive approach that only the image region of the magnetic resonance image data that is of interest to a user is supplied, for example displayed, for the user.

In an embodiment, the image region that is provided maps the first recording region. In particular, the image region corresponds in terms of its position, in particular its spatial positioning, with respect to the examination object to the first recording region. The image region also corresponds, in particular with respect to geometry, to the first recording region. The image region also corresponds, in particular in one measurement in at least one dimension, preferably in two dimensions or in all three dimensions, to the first recording region. The image region that is finally supplied as an output can therefore correspond to the section of the magnetic resonance image data that is chosen as the first recording region for mapping. In this way the image region of the magnetic resonance image data which is actually of interest to the user is mapped for the user since it has been chosen by the user individually. Only the image region that maps the first recording region is supplied. The part of the magnetic resonance image data that maps the second recording region and not the first recording region can therefore be discarded during or after the reconstruction of the magnetic resonance image data. During diagnosis the user can therefore concentrate on the image region of the magnetic resonance image data of interest, which the user determined manually as the first recording region.

In an embodiment, the image region that is supplied as an output matches the first recording region in all of its dimensions and in its spatial positioning. Therefore, exactly the first recording region is mapped in the image region of the magnetic resonance image data that is supplied as an output.

In another embodiment, the first recording region is a sub-part of the second recording region. The second recording region thus is larger than the first recording region, in particular in at least one extent in one dimension, preferably in two extents in two dimensions. The first recording region is preferably completely contained in the second recording region. As described below, the first recording region is expanded in at least one direction, preferably in two directions, resulting in the cube-shaped second recording region. Because the first recording region is a sub-part of the second recording region, it can be ensured that the magnetic resonance image data actually maps at least the first recording region that is of particular interest to a user.

In another embodiment, the first cuboidal recording region has a first extent in a first direction, a second extent in a second direction and a third extent in a third direction, wherein the first extent is longer than the second extent and the third extent, wherein the first recording region is adjusted for automatic determination of the second recording region such that the second extent and the third extent are adjusted to the first extent. The first direction and/or the second direction and/or the third direction can be along a readout direction and/or a phase coding direction and/or a slice direction of the magnetic resonance sequence used to acquire the magnetic resonance scan data. An adjusted second extent, in particular, is generated when the second extent is adjusted. An adjusted third extent, in particular, is generated when the third extent is adjusted. That the second extent and the third extent are adjusted to the first extent means, in particular, that the adjusted second extent and the adjusted second extent each match the first extent. The second recording region can then have the first extent in the first direction, the second adjusted extent in the second direction and the third adjusted extent in the third direction. In other words, the cuboidal first recording region has one long side in the first direction that has the first extent as its length. The first recording region has two shorter sides which are shorter than the long side. The two shorter sides are then arranged in the second direction and third direction and have the second extent and the third extent as their length. When the first recording region is adjusted to create the cube-shaped second recording region, the side length of the two shorter sides is then adjusted to the side length of the first side. In this way the first recording region is enlarged to generate the cube-shaped second recording region. It can therefore be particularly easily ensured that the second recording region is cube-shaped and completely encompasses the first recording region. The first extent of the first recording region advantageously remains constant when the first recording region is adjusted. Instead, the other extents of the first recording region in the other two directions are adjusted to the longest extent of the first recording region in the first direction.

In another embodiment, adjustment of the second extent to the first extent comprises a lengthening of the second extent by a second extension factor, wherein the second extension factor is a ratio between the first extent and the second extent. The second extension factor for one direction indicates by which factor the spatial extent of the first recording region must be extended in the second direction for the spatial extent of the second recording region of the second direction to be produced. In other words, the extension factor for the second direction indicates by which factor the spatial extent of the second recording region is increased in this direction with respect to the spatial extent of the first recording region. The second extension factor is therefore greater than one. In the second direction, the second recording region can in this way have an extent which matches the extent of the first recording region in the first direction. The second extension factor can also be automatically adjusted if the user makes a change at a user interface to the first recording region in order to ensure that the second recording region remains cube-shaped.

In another embodiment, adjustment of the third extent to the first extent comprises a lengthening of the third extent by a third extension factor, wherein the third extension factor is a ratio between the first extent and the third extent. The properties, described in the preceding paragraph, of the second extension factor can also be used analogously for the third extension factor. The second recording region can in this way have an extent in the third direction that matches the extent of the first recording region in the first direction.

The inventive magnetic resonance apparatus has an input interface, a data acquisition scanner, an output interface and a computer that has a determining processor and a reconstruction processor, wherein the magnetic resonance apparatus is designed to implement the inventive method.

In this way the inventive magnetic resonances apparatus is designed to implement a method for magnetic resonance imaging an examination object. The input interface is designed for the selection of a first recording region that is cuboidal. The determining processor is configured for automatic determination of a second recording region, which represents an adjustment of the first recording region such that the second recording region is cube-shaped. The data acquisition scanner is designed for the acquisition of magnetic resonance scan data from the entire second recording region. The reconstruction processor is designed for the reconstruction of magnetic resonance image data from the magnetic resonance scan data. The output interface is designed for supplying an image region of the magnetic resonance image data as an output.

The invention also encompasses a non-transitory, computer-readable storage medium that can be loaded directly into a memory of the programmable arithmetic processor of a magnetic resonance apparatus, and is encoded with program code that cause the processor to implement the inventive method when the program code is executed in the arithmetic processor of the magnetic resonance apparatus. The inventive method can be carried out quickly, robustly and in a manner that can be repeated in an identical manner. The arithmetic processor must have certain components, such as an appropriate main memory, an appropriate graphics card or an appropriate logic unit, so the respective method steps can be carried out efficiently. Examples of electronically readable data carriers are a DVD, magnetic tape or a USB stick, on which electronically readable control information, in particular software (cf. above), is stored.

The advantages of the inventive magnetic resonance apparatus and of the inventive storage medium substantially correspond to the advantages of the inventive method, which have been stated above in detail. Features, advantages or alternative embodiments mentioned in this connection are similarly applicable to all aspects of the invention. The functional features of the method are formed by appropriate physical modules, in particular by hardware modules.

BRIEF DESCRIPTION OF THE DRAWINGS

FIG. 1 shows an inventive magnetic resonance device in a schematic illustration.

FIG. 2 is a flowchart of a first embodiment of the inventive method.

FIG. 3 is a flowchart of a second embodiment of the inventive method.

FIG. 4 shows an exemplary illustration of the inventive approach.

DESCRIPTION OF THE PREFERRED EMBODIMENTS

FIG. 1 schematically shows an inventive magnetic resonance apparatus 11. The magnetic resonance apparatus 11 has a detector unit formed by a magnet unit 13, having a basic field magnet 17 for generating a strong and constant basic magnetic field 18. In addition, the magnetic resonance apparatus 11 has a cylindrical patient-receiving region 14 for receiving an examination object 15, in the present case a patient, with the patient-receiving region 14 being cylindrically surrounded in a circumferential direction by the magnet unit 13. The patient 15 can be moved by a patient-positioning device 16 of the magnetic resonance apparatus 11 into the patient-receiving region 14. The patient-positioning device 16 has for this purpose an examination table arranged so as to move inside the magnet unit 11. The magnet unit 13 is shielded from the outside by a housing shell 31.

The magnet unit 13 also has a gradient coil arrangement 19 for generating magnetic field gradients that are used for spatial encoding during imaging. The gradient coil arrangement 19 is controlled by a gradient control processor 28. The magnet unit 13 also has a radio-frequency antenna arrangement 20, which is designed in the illustrated case as a body coil permanently integrated in the magnetic resonance scanner 13, and a radio-frequency antenna control processor 29 for exciting nuclear spins in the patient 13 so as to deviate from the polarization that is established in the basic magnetic field 18 generated by the basic field magnet 17. The radio-frequency antenna arrangement 20 is controlled by the radio-frequency antenna control processor 29 and radiates radio-frequency magnetic resonance sequences into an examination volume that is essentially formed by the patient-receiving region 14. The radio-frequency antenna arrangement 20 is also designed to receive magnetic resonance signals from the patient 15.

For controlling the basic magnet 17, the gradient control processor 28 and the radio-frequency antenna control processor 29, the magnetic resonance apparatus 11 has a computer 24. The computer 24 centrally controls the magnetic resonance apparatus 11, such as, for example, for carrying out a predetermined imaging gradient echo sequence. Control information, such as imaging parameters, and reconstructed magnetic resonance images, can be supplied for a user via an output interface, in the present case a display monitor 25, of the magnetic resonance apparatus 11. The output interface can alternatively implement storage of the magnetic resonance image data on a database. In addition, the magnetic resonance apparatus 11 has an input interface 26 by which the user can enter information and/or parameters during a measuring process. The computer 24 can include the gradient control processor 28 and/or the radio-frequency antenna control processor 29 and/or the display monitor 25 and/or the input interface 26.

In the illustrated case the computer 24 has a determining processor 33 and a reconstruction processor 34. The magnetic resonance apparatus 11 also has a data acquisition scanner 32. In the present case the data acquisition scanner 32 is formed by the magnet unit 13 together with the radio-frequency antenna control processor 29 and the gradient control processor 28. The magnetic resonance apparatus 11, together with the data acquisition scanner 32, computer 24, input interface 26 and the monitor 25, is therefore configured to carry out an inventive method for magnetic resonance imaging.

The illustrated magnetic resonance apparatus 11 can of course have further components which magnetic resonance apparatuses conventionally have. The general operation of a magnetic resonance apparatus 11 is known to those skilled in the art, so a detailed description of the further components is not necessary herein.

FIG. 2 is a flowchart of a first embodiment of an inventive method for magnetic resonance imaging the examination object 15 by means of the magnetic resonance apparatus 11.

In a first method step 40 a first recording region, which is cuboidal, is chosen by the input interface 26.

In a further method step 41 a second recording region is automatically determined by means of the determining unit 33, wherein the second recording region represents an adjustment of the first recording region such that the second recording region is cube-shaped.

In a further method step 42 magnetic resonance scan data is acquired from the entire second recording region by means of the data acquisition scanner 32.

In a further method step 43 magnetic resonance image data is reconstructed from the magnetic resonance scan data by the reconstruction processor 34.

In a further method step 44 an image region of the magnetic resonance image data is provided by the display monitor 25.

FIG. 3 is a flowchart of a second embodiment of an inventive method for magnetic resonance imaging.

The following description is essentially limited to the differences from the exemplary embodiment in FIG. 2, with reference being made in respect of unchanging method steps to the description of the exemplary embodiment in FIG. 2. Method steps that essentially stay the same are basically numbered with the same reference numerals.

The embodiment of the inventive method shown in FIG. 3 essentially comprises method steps 40, 41, 42, 43, 44 of the first embodiment of the inventive method according to FIG. 2. In addition, the embodiment of the inventive method shown in FIG. 3 comprises additional method steps and substeps. An alternative method sequence to FIG. 3 is also conceivable, which has just some of the additional method steps and/or substeps shown in FIG. 2. Of course, an alternative method sequence to FIG. 3 can have additional method steps and/or substeps.

The cuboidal first recording region FOV1, which is chosen in the first method step, comprises a first extent L1 in a first direction, a second extent L2 in a second direction and a third extent L3 in a third direction. Without limiting the generality, the first extent L1 should be longer than the second extent L2 and the third extent L3.

FIG. 4 shows an exemplary example to illustrate the inventive approach. Reference is made to the fact that the inventive approach is not limited to the use according to the example shown in FIG. 4. For the sake of clarity FIG. 4 also shows just one adjustment of a two-dimensional recording region. The inventive method is primarily used, however, for three-dimensional recording regions. In this way an extension of the example shown in FIG. 4 by a further dimension is preferred.

FIG. 4 shows a coronal slice representing a head region of the examination object 15. In this way the first direction is arranged in the axial direction in a head-to-foot direction. The second direction is arranged in a sagittal direction perpendicular to the first direction. The illustrated slice can be recorded, for example, in a topogram (localizer). The cuboidal first recording region FOV1 is chosen such that the head of the examination object 15 is completely covered by the first recording region FOV1. The longer first extent L1 of the first recording region FOV1 is therefore arranged in a longitudinal direction of the head, in a head-to-foot direction, and the shorter second extent L2 of the first recording region FOV2 is arranged in a transverse direction of the head, perpendicular to the head-to-foot direction.

The second recording region FOV2 is then determined in a further method step 41 such that, with an adjustment of the first recording region FOV1, the second extent L2 and the third extent L3 are adjusted to the first extent L1. An adjusted second extent AL2 and an adjusted third extent AL3 are generated for the second recording region FOV2 in the process. In particular, the adjusted second extent AL2 and the adjusted third extent AL3 are equal to the first extent L1. The second recording region FOV2 has the first extent L1 which is retained with respect to the first recording region FOV1. In this way the first recording region FOV1 can be a section of the second recording region FOV2.

The adjustment of the second extent L2 to the first extent L1 preferably comprises a lengthening of the second extent L2 by a second extension factor F2, wherein the second extension factor F2 is a ratio between the first extent L1 and the second extent L2. For this purpose, the second extension factor F2 is preferably calculated by taking into account the first extent L1 and the second extent L2, before the second extent L2 is adjusted to the adjusted second extent AL2 for generation of the second recording region FOV2. In the same way the adjustment of the third extent L3 to the first extent L1 can comprise a lengthening of the third extent L3 by a third extension factor F3, wherein the third extension factor F3 is a ratio between the first extent L1 and the third extent L3.

In relation to the example in FIG. 4, the second extent L2 of the first recording region FOV1 was then increased to generate the adjusted extent AL2 of the second recording region FOV2. For the second recording region FOV2 there is therefore a square slice containing the head of the examination object 15 and a surrounding region of the head, with the surrounding region primarily covering air. The extension of the second extent L2 occurred by a factor F2, wherein the following applies for the calculation of the factor F2:

$$F2 = \frac{L1}{L2}$$

In this way the adjusted second extent AL2 should be calculated such that:

$$AL2 = L2 * F2 = L2 * \frac{L1}{L2} = L1$$

If it is then assumed that there are slices in a sagittal direction 320, the extension of FOV2 with respect to FOV1 in the second direction leads to potentially 70-80 slices mapping regions that are not relevant, for example air. With a direct output of magnetic resonance image data, which maps the second recording region FOV2, this leads to a person making the diagnosis having to first of all scroll through a large number of slices until he or she arrives at the relevant head region in the magnetic resonance image data. The slices that are not relevant are located at the start and end of the slice stack in the sagittal direction. This fact can be regarded as annoying. At the same time, a large volume of data without clinical relevance would be generated. The same problem can also occur in the coronal direction. For the sake of clarity this is not shown in FIG. 4.

In this way the magnetic resonance scan data is acquired in a further method step 42 from the entire second examination region FOV2 and magnetic resonance image data is reconstructed in a further method step 43 from the magnetic resonance scan data. In particular, a magnetic resonance sequence S which requires a cube-shaped recording region is used to acquire the magnetic resonance scan data.

Not all of the magnetic resonance image data is then supplied, for example displayed on the display unit 25 or stored in a database, in a further method step 44. Instead only some of the magnetic resonance image data, namely one image region of the magnetic resonance image data, is supplied. The image region that is supplied preferably maps the first recording region FOV1. In particular, the image region that is supplied is corresponds in all of its dimensions and in its spatial positioning to the first recording region FOV1.

In this way, according to the example in FIG. 4, the user is only supplied with magnetic resonance image data which maps the head region of the examination object 15. The user can concentrate on the relevant head region when making a diagnosis. This is especially expedient since, when choosing the first recording region FOV1, the user chose precisely the head region for mapping in the magnetic resonance image data. The extension to the second recording region FOV2 for acquiring the magnetic resonance scan data was only carried out since a magnetic resonance sequence, which requires a square recording region, for example a PETRA sequence, was used to acquire the magnetic resonance scan data. The region in broken lines in FIG. 4, which represents the extension of the second recording region FOV2 with respect to the first recording region FOV1, so the cube shape condition is met for the second recording region FOV2, is not supplied to the user; it is, for example, cut out or masked.

The method steps of the inventive method shown in FIGS. 2-4 are carried out by the computer 24. For this purpose, the computer 24, the requisite software and/or computer programs are stored in an accessible memory. The software and/or computer programs have program code configured to carry out the inventive method when the computer program and/or the software are executed in the computer 24 by a processor of the computer 24.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a magnetic resonance imaging apparatus comprising:
   providing an electronic designation to a computer that selects a first recording region, which is cuboidal, of an examination subject;
   in said computer, automatically determining a second recording region within said subject that is an adjustment of the first recording region, with said second recording region being cube-shaped;
   embodying said second recording region in a magnetic resonance data acquisition sequence and operating a magnetic resonance scanner with said magnetic resonance sequence to acquire magnetic resonance scan data from an entirety of said second recording region;
   providing said magnetic resonance scan data to an image reconstruction computer and, in said image reconstruction computer, reconstructing magnetic resonance image data from the magnetic resonance scan data; and
   making an image region of the magnetic resonance image data available in electronic form as a data file from said image reconstruction computer.

2. A method as claimed in claim 1 comprising generating said magnetic resonance sequence as a magnetic resonance sequence that requires a cube-shaped recording region.

3. A method as claimed in claim 1 comprising providing, as said image region from said image reconstruction computer, an image region that maps said first recording region.

4. A method as claimed in claim 1 comprising providing, as said image region, an image region corresponding in all dimensions and in spatial positioning with said first recording region.

5. A method as claimed in claim 1 wherein said computer automatically determines said second recording region so that said first recording region is a section of said second recording region.

6. A method as claimed in claim 1 wherein said first recording region has a first extent in a first direction, as second extent in a second direction, and a third extent in a third direction, wherein said first extent is longer than said second extent and said third extent, and comprising, in said computer, adjusting said first recording region for automatic determination of said second recording region so that said second extent and said third extent are adjusted to the first extent.

7. A method as claimed in claim 6 comprising adjusting said second extent to said first extent by lengthening the second extent by a second extension factor, said second extension factor being a ratio of said first extent and said second extent.

8. A method as claimed in claim 6 comprising adjusting said third extent to said first extent by lengthening said third extent by a third extension factor that is a ratio between said first extent and said third extent.

9. A magnetic resonance apparatus comprising:
   a magnetic resonance scanner;
   a computer provided with an electronic designation that selects a first recording region, which is cuboidal, of an examination subject;
   said computer being configured to automatically determine a second recording region within said subject that is an adjustment of the first recording region, with said second recording region being cube-shaped;
   said computer being configured to embody said second recording region in a magnetic resonance data acquisition sequence and to operate the magnetic resonance scanner with said magnetic resonance sequence to acquire magnetic resonance scan data from an entirety of said second recording region;
   said computer being configured to reconstruct magnetic resonance image data from the magnetic resonance scan data; and
   said computer being configured to make an image region of the magnetic resonance image data available in electronic form as a data file from said computer.

10. A non-transitory, computer-readable data storage medium encoded with programming instructions, said storage medium being loaded into a control and evaluation computer of a magnetic resonance apparatus that comprises a magnetic resonance scanner, said programming instructions causing said control and evaluation computer to:
   receive an electronic designation to a computer that selects a first recording region, which is cuboidal, of an examination subject;
   automatically determine a second recording region within said subject that is an adjustment of the first recording region, with said second recording region being cube-shaped;

embody said second recording region in a magnetic resonance data acquisition sequence and operate a magnetic resonance scanner with said magnetic resonance sequence to acquire magnetic resonance scan data from an entirety of said second recording region;

reconstruct magnetic resonance image data from the magnetic resonance scan data; and make an image region of the magnetic resonance image data available in electronic form as a data file from said control and evaluation computer.

* * * * *